US008679152B2

(12) United States Patent  
Viola

(10) Patent No.: US 8,679,152 B2  
(45) Date of Patent: Mar. 25, 2014

(54) SURGICAL MESH MAKER

(75) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 263 days.

(21) Appl. No.: 12/825,645

(22) Filed: Jun. 29, 2010

(65) Prior Publication Data

US 2011/0319915 A1 Dec. 29, 2011

(51) Int. Cl.
*A61B 17/04* (2006.01)
(52) U.S. Cl.
USPC ............................ 606/214; 606/151; 606/213
(58) Field of Classification Search
None
See application file for complete search history.

(56) References Cited

U.S. PATENT DOCUMENTS

| | | | | |
|---|---|---|---|---|
| 2,563,048 A * | 8/1951 | Liebelt et al. | ................ | 401/197 |
| 2,563,049 A * | 8/1951 | Liebelt et al. | ................ | 401/197 |
| 2,565,743 A * | 8/1951 | Schaefer | ...................... | 401/197 |
| 4,648,732 A * | 3/1987 | Smialkowski | ............... | 401/196 |
| 5,464,403 A | 11/1995 | Kieturakis et al. | | |
| 5,749,968 A * | 5/1998 | Melanson et al. | ........... | 118/300 |
| 6,156,003 A | 12/2000 | Suresh | | |
| 6,394,982 B1 | 5/2002 | Ehrenfels | | |
| 6,425,704 B2 * | 7/2002 | Voiers et al. | .................. | 401/196 |
| 6,699,262 B2 * | 3/2004 | Redmond et al. | ............. | 606/213 |
| 7,867,222 B1 * | 1/2011 | Tilton et al. | ........................ | 606/1 |
| 7,946,453 B2 * | 5/2011 | Voegele et al. | ............... | 222/134 |
| 8,118,508 B2 * | 2/2012 | Goodman et al. | ........... | 401/133 |
| 8,123,423 B2 * | 2/2012 | Houde et al. | .................. | 401/205 |
| 2008/0114315 A1 * | 5/2008 | Voegele et al. | ............... | 604/311 |
| 2008/0131190 A1 | 6/2008 | Goodman et al. | | |
| 2008/0302487 A1 | 12/2008 | Goodman et al. | | |
| 2009/0270884 A1 * | 10/2009 | Hake | ............................. | 606/139 |

FOREIGN PATENT DOCUMENTS

WO WO 97/48351 A1 12/1997

OTHER PUBLICATIONS

European Search Report dated Jun. 14, 2013 in corresponding European Application No. 11250617.

* cited by examiner

*Primary Examiner* — Melanie Tyson
*Assistant Examiner* — Todd J Scherbel

(57) ABSTRACT

A surgical mesh maker applicator for applying an in situ forming material to subdermal tissue is disclosed and includes a handle and an outer tube extending from the handle. The outer tube defines a longitudinal axis and a longitudinal slot along a distal portion of the outer tube. An inner tube containing a pattern extends at least partially through the outer tube. A rotational mechanism rotates the inner tube with respect to the longitudinal axis to dispense the in situ forming material into a patterned structure for strengthening the subdermal tissue.

17 Claims, 15 Drawing Sheets

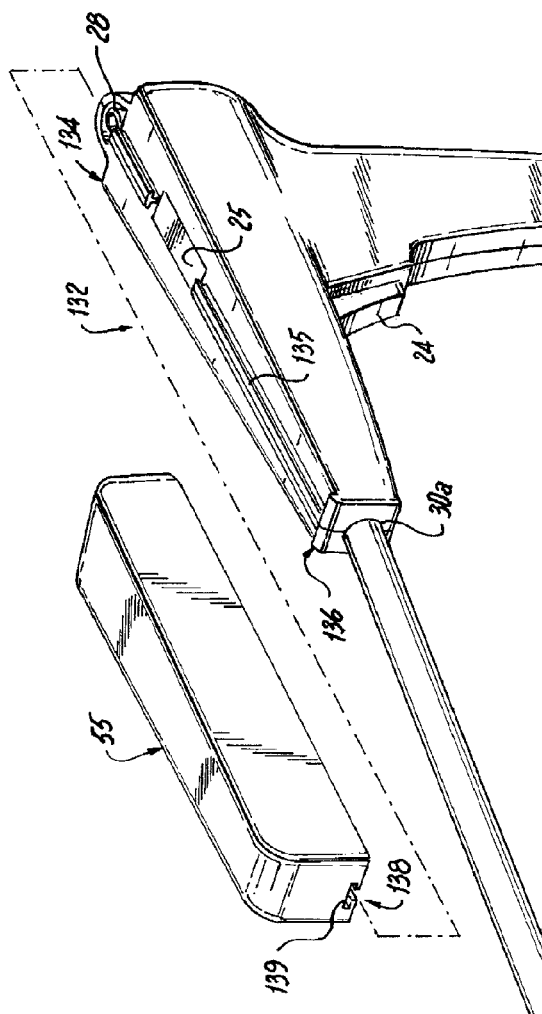
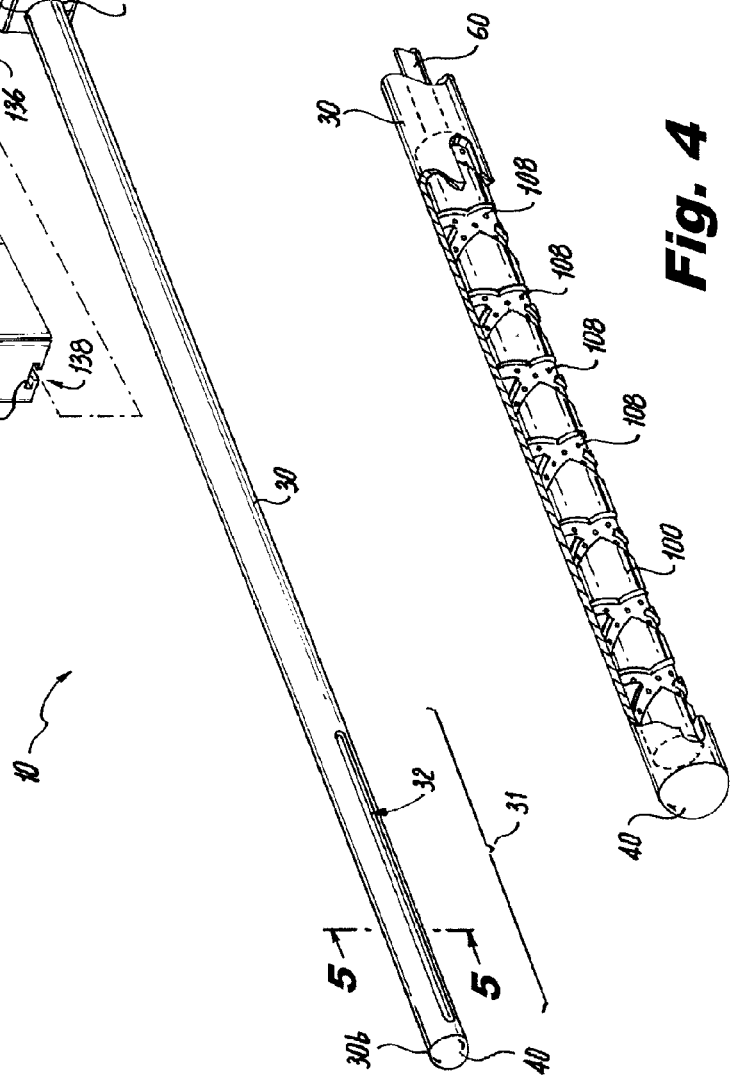
Fig. 1
Fig. 4

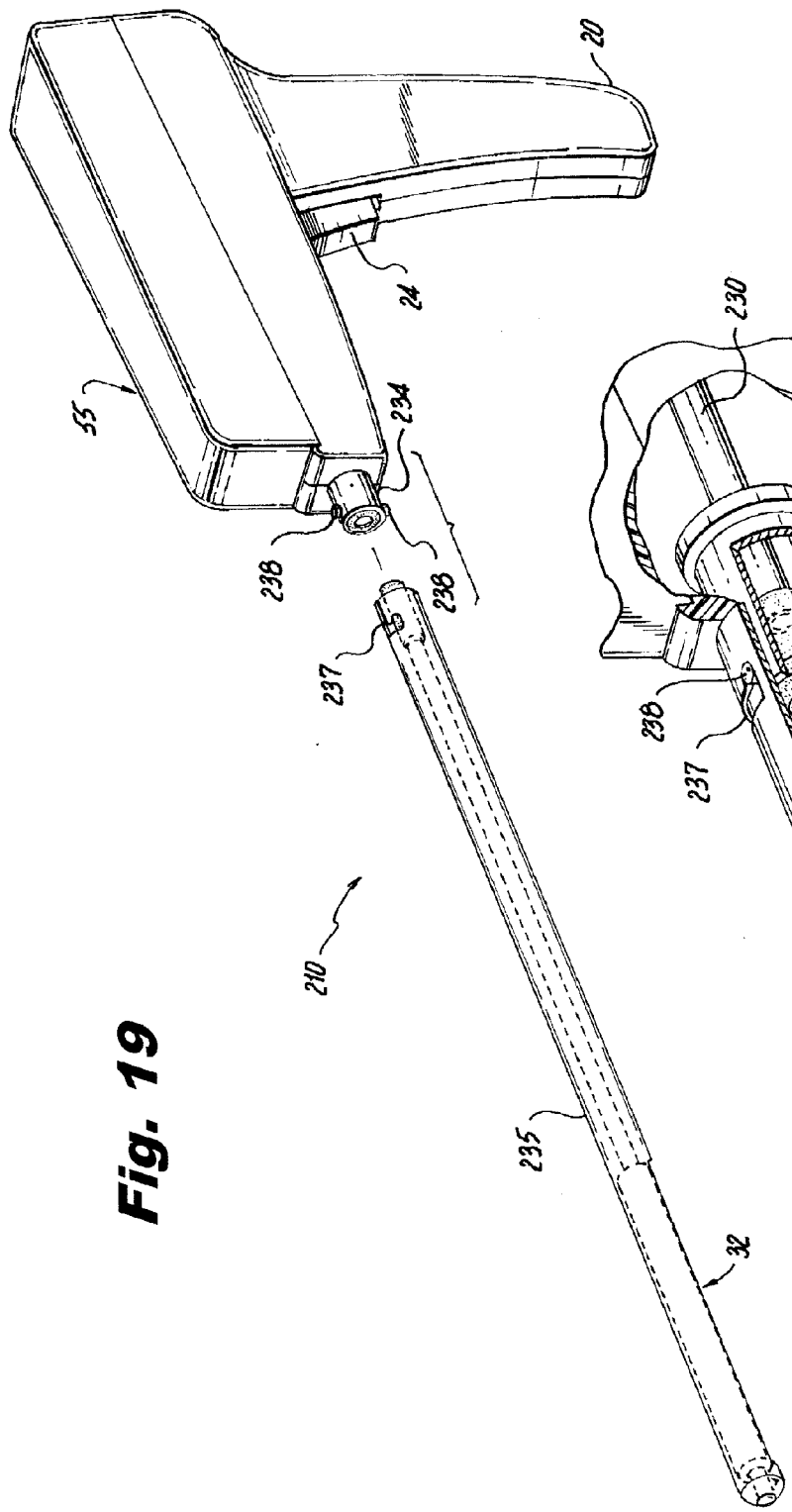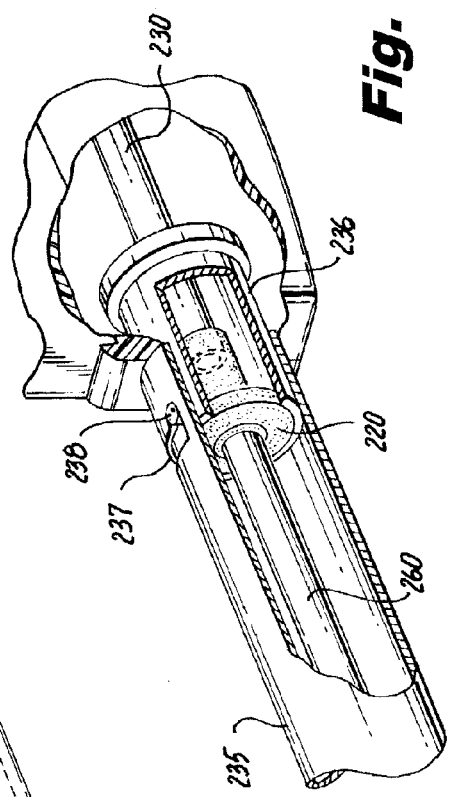

SURGICAL MESH MAKER

BACKGROUND

1. Technical Field

This application generally relates to the field of hernia repair. More particularly, the present disclosure relates to a method and a device for applying an in-situ forming material to sub-dermal tissue to create surgical meshes.

2. Related Art

Surgical repair of tissues using materials inserted into the body commonly includes repair of a defect in the abdominal wall, or hernia. A hernia can generally be described as a protrusion of an organ or bodily part through connective tissue or through the wall of the cavity in which it is normally enclosed. These abnormalities can be categorized with respect to the anatomic position of the hernia. An inguinal hernia is the most common type of hernia, which describes a hernia of the groin, wherein abdominal contents (e.g., intestine) can protrude from the abdomen through a defect in the inguinal canal. Inguinal hernias can further be described as "indirect" or "direct". Indirect inguinal hernias are defects within the apex of the inguinal canal, occurring at the internal ring. Direct hernias are defects within the back wall of the inguinal canal, medial to the spermatic cord. Other abdominal hernias include; femoral hernias, which occur below the groin crease, umbilical hernias, which occur at the umbilical cord, ventral hernias, which occur at the midline of the abdomen, and diaphragmatic hernias, which occur high in the abdominal cavity near the chest. Moreover, hernias can also result from a prior incision that has not properly healed and has reopened, which is referred to as incisional hernias.

The conventional herniorrhaphy surgical procedure for umbilical and ventral hernias comprises creating a single incision several inches in length through the abdominal wall and into the abdominal cavity, which can enable the identification of the defect and hernia contents. In inguinal hernia repair, the hernia can be identified from the weakness that comes from the abdominal cavity. If the hernia is reducible, the herniated tissues can be pushed back into the abdominal cavity, and the defect can be fixed by fixedly attaching a prosthetic reinforcing material (e.g., mesh) or by closing the defect primarily utilizing sutures.

As less invasive surgical techniques are advancing in the field of hernia repair, there is a growing need for innovative laparoscopic compatible devices that alleviate shortcomings in the art and provide novel solutions for laparoscopic hernia repair. Disclosed herein are devices and methods for their use that provide such needed innovations.

SUMMARY

The present disclosure is directed to surgical mesh maker applicator for applying an in situ forming material to subdermal tissue. The surgical mesh maker applicator has a handle that includes an outer tube having an elongated or longitudinal slot along a distal portion of the outer tube. An inner tube is movably disposed in the outer tube, the inner tube including a plurality of openings located on a surface thereof. An in situ forming material is fluidly coupled to the inner tube. Movement of the inner tube relative to the outer tube dispenses a quantity of the in situ forming material through the elongated slot in a patterned structure, e.g., a mesh, for strengthening the subdermal tissue.

In some embodiments, the inner tube rotationally rotates relative to the outer tube and has a predetermined pattern that dispenses the in situ forming material into a mesh. The inner tube contains a series of ports that provide a path from the inner passageway to the predetermined pattern.

The surgical mesh maker applicator includes a cartridge. The cartridge includes a collapsible container configured to retain the in situ forming material therein.

The cartridge includes a receiving mechanism configured to removably connect with a retention mechanism. As disclosed, the retention mechanism is a projecting slide and the receiving mechanism is a recess configured to accept the projecting slide. The retention mechanism has a stop member. The stop member limits placement of the cartridge with respect to the housing.

The surgical mesh maker applicator includes an actuation mechanism to impart movement of the in situ forming material at least partially through the inner tube. The surgical mesh maker applicator includes a trigger at least partially located within the handle and operatively connected with the actuation mechanism.

The cartridge includes a receptor operatively connected with the actuation mechanism and the handle includes a transmitter operatively connected with the trigger. The transmitter and the receptor are in communication with each other to provide a signal to the actuation mechanism.

The surgical mesh maker applicator includes an in situ forming material. The in situ forming material may be an isocyanate-based adhesive, a cyanoacrylate adhesive, an epoxy-based adhesive, a light cured adhesive, an adhesive based on CLICK chemistry, or a two-component adhesives based of nucleophilic and electrophylic components.

In still another embodiment, the outer tube has a first tubular portion and a second tubular portion. The first tubular portion is at least partially supported by the handle and the second tubular portion is removably joinable with the first tubular portion to allow replacement of the second tubular portion.

A method of use of the surgical mesh maker applicator to repair weakened sub-denial tissue of a patient is also provided. The surgeon is provided with the surgical mesh maker applicator. The internal tissue cavity of the patient is insufflated. The surgeon creates an incision in the dermal tissue layer of the patient. The outer tube of the surgical mesh maker applicator is inserted into the incision through a surgical portal. The in situ forming material is applied to the subdermal tissue in the form of a patterned structure.

A cartridge for use with a surgical mesh maker applicator is also provided. The cartridge includes a housing, an in situ forming material, and a container and an actuation mechanism at least partially contained within the housing. The container retains the in situ forming material therein. The actuation mechanism provides movement of the in situ forming material. A coupling mechanism removably attaches the housing to the surgical mesh maker applicator.

In another embodiment, a surgical mesh maker applicator includes a handle, a trigger movably connected with the handle, and an outer tube. The outer tube extends from the handle and defines a longitudinal axis and a longitudinal slot along a distal portion of the outer tube. A first feeder tube and a second feeder tube extend at least partially through the outer tube. The first feeder tube and the second feeder tube are parallel to each other. An oscillating mechanism moves at least one of the feeder tubes with respect to the other feeder tube along the longitudinal axis. An arm extends from each of the feeder tubes. Each of the arms defines a central passageway and a series of nozzles.

The series of nozzles are aligned linearly along an outer surface of the arm and define an aperture connected with the central passageway. Each of the series of nozzles is located along respective arms to be in relatively close proximity to the other of the series of nozzles. Each of the series of nozzles may be removable and replaceable to provide a variety of shaped apertures.

These and other embodiments of the present disclosure will be described in greater detail below with reference to the appended figures.

BRIEF DESCRIPTION OF THE DRAWINGS

The accompanying drawings, which are incorporated in and form part of the specification, illustrate the present disclosure when viewed with reference to the description, wherein:

FIG. 1 is an exploded perspective view of the surgical mesh maker applicator of FIG. 1 with the cartridge separated from the handle;

FIG. 4 is a partial cut away view of a contoured inner tube and outer tube in accordance with the principles of the present disclosure;

FIG. 19 an exploded view of another embodiment of the surgical mesh maker applicator having a removable portion;

FIG. 20 is an enlarged partial cut-away view of the removable applicator installed on the surgical mesh maker applicator of FIG. 19;

Figure 2:
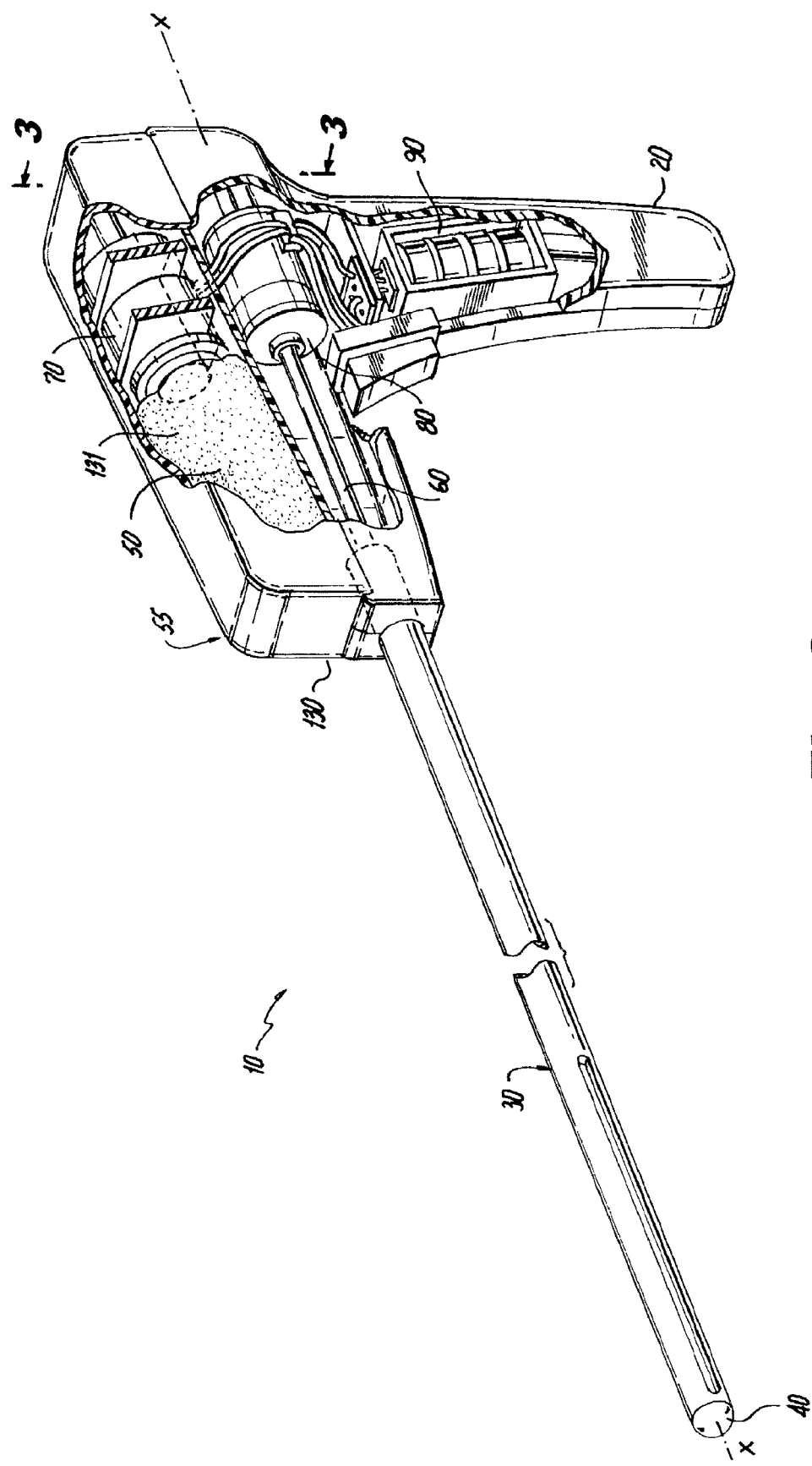
FIG. 2 is a partial cut away view of the in situ surgical mesh maker applicator of FIG. 1.

Other features of the present disclosure will become apparent from the following detailed description taken in conjunction with the accompanying drawings, which illustrate, by way of example, the principles of the present disclosure.

DETAILED DESCRIPTION OF THE EMBODIMENTS

Embodiments of the presently disclosed surgical mesh maker applicator and a method for use are described in detail with reference to the drawings, in which like reference numerals designate identical or corresponding elements in each of the several views. As used herein, the term "distal" refers to that portion of the apparatus, or component thereof, farther from the user while the term "proximal" refers to that portion of the apparatus or component thereof, closer to the user.

Referring now to the drawings, wherein like reference numerals identify identical or similar structural elements of the subject device throughout the several views, there is illustrated in FIG. 1 a surgical mesh maker applicator 10, designated generally by reference numeral 10.

The present disclosure is directed to a surgical mesh maker applicator 10 for applying an in situ forming material to sub-dermal tissue layer and includes a handle 20, an outer tube 30, a cap 40, and a cartridge 55. A proximal end 30a of the outer tube 30 is supported by and extends distally from the handle 20. The outer tube 30 defines a longitudinal 'X' axis (FIG. 2) and a longitudinal slot 32 along a distal portion 31 of the outer tube 30. The cap 40 mates with a distal end 30b of the outer tube 30 to form a seal with the outer tube 30 and to close the distal end 30b.

The surgical mesh maker applicator 10 has a coupling mechanism 132, which includes a receiving mechanism 138 along one side of the cartridge 55 to removably connect with a retention mechanism 134 on the handle 20. As disclosed, the retention mechanism 134 is a projecting slide rail 135 and the receiving mechanism 138 is a recess 139 configured to accept the projecting slide rail 135. The retention mechanism 134 includes a stop member 136. The stop member 136 limits placement of the cartridge 55 with respect to the handle 20.

With additional reference to FIG. 2, the cartridge 55 includes a housing 130, an actuation mechanism 70, and a collapsible container 131. An in situ forming material 50 is contained within the collapsible container 131. The in situ forming material 50 may be an isocyanate-based adhesive, a cyanoacrylate adhesive, an epoxy-based adhesive, a light cured adhesive, an adhesive based on CLICK chemistry, or a two-component adhesives based of nucleophilic and electrophylic components. The in situ forming material 50 may be a type of material that cures upon activation by an agent. Further, the in situ material 50 may contain additives to increase the tensile strength and or the rigidity of the material.

Figure 3:
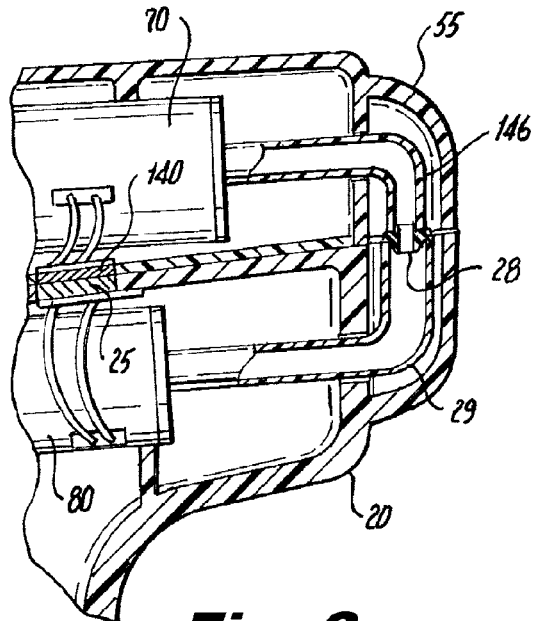
FIG. 3 is a side cross-sectional view of the surgical mesh maker applicator of FIG. 2 taken along section line 3-3.
Figure 5:
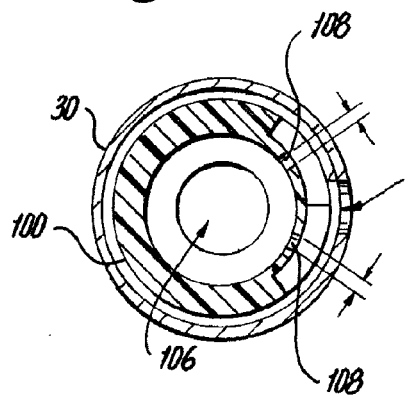
FIG. 5 is a front cross-sectional view of the inner tube and outer tube taken along section line 5-5 of FIG. 1.
Figure 6:
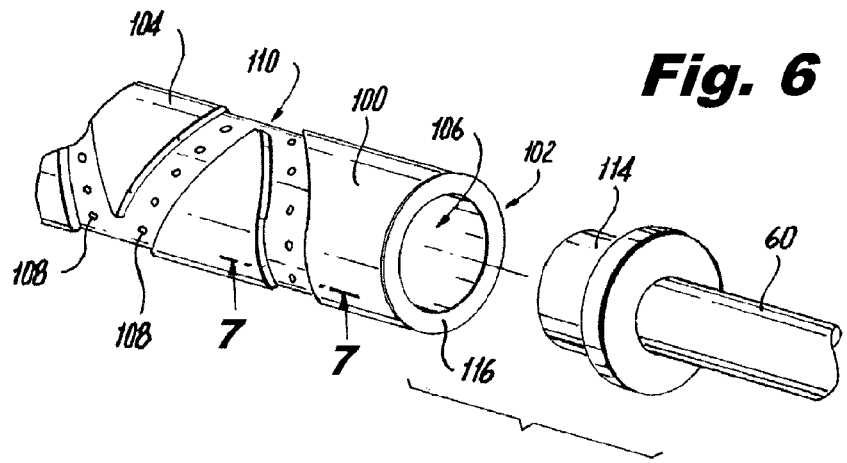
FIG. 6 is an enlarged perspective view of the inner tube in accordance with the principles of the present disclosure.

The actuation mechanism 70 and the collapsible container 131 are at least partially located within the housing 130 of the cartridge 55. With additional reference to FIG. 3, the cartridge 55 includes a receptor 140 operatively connected with the actuation mechanism 70 and the handle 20 includes a transmitter 25 operatively connected with a trigger 24. The trigger 24 is at least partially located within and supported by the handle 20. The trigger 24 is operatively connected with the actuation mechanism 70. The transmitter 25 and the receptor 140 are in communication with each other.

The cartridge 55 includes a cartridge duct 146. The cartridge duct provides a pathway for in situ forming material 50 from the collapsible container 131 to a coupling 28. The coupling 28 forms a seal between the cartridge duct 146 and a housing duct 29 located within the handle 20. The coupling 28 may be a one-way valve that allows the cartridge 55 to be removed from the handle 20 without leakage of the in situ forming material 50. The housing duct 29 is operatively connected with an inner tube 60.

Actuation of the trigger 24 provides a signal to the transmitter 25. The transmitter conveys the signal to the receptor 140. The receptor 140 then sends the signal to actuate the actuation mechanism 70. The actuation mechanism 70 transfers the in situ forming material 50 from the cartridge 55 to the inner tube 60.

With continued reference to FIG. 2, the inner tube 60 extends at least partially through the outer tube 30 and is connected with a rotational mechanism 80. The rotational mechanism 80 and a battery pack 90 are supported between a right hand side 21 (FIG. 1) and a left hand side 22 (FIG. 1) of the handle 20. The battery pack 90 provides electrical power to both the actuation mechanism 70 and the rotational mechanism 80. The rotational mechanism 80 rotates the inner tube 60 with respect to the longitudinal 'X' axis.

With reference to FIGS. 4-7, an inner member or roller 100 extends distally from the inner tube 60. The inner tube 60 includes a neck 114 sized and shaped to mate with a yoke 116 defined by the roller 100. The coupling of the yoke 116 about the neck 114 connects the inner tube 60 and the inner member or roller 100, such that any rotational motion of the inner tube 60 is translated into and causes the inner member or roller 100 to also rotate.

The inner member or roller 100 is an elongated tubular member 102 that defines an inner passageway 106, a series of ports 108, and a recessed pattern 110 along an outer surface 104. The inner passageway 106 provides longitudinal passage of the in situ forming material 50 through the inner member or roller 100. The series of ports 108 provide a radial path from the inner passageway 106 to the recessed pattern 110.

Figure 7:
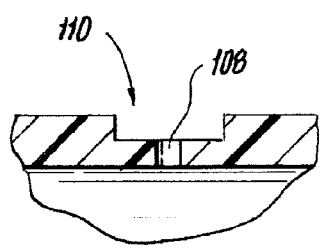
FIG. 7 is an enlarged cross-sectional view of the inner tube in accordance with the principles of the present disclosure taken along section line 7-7 of FIG. 6 illustrating a rectangular cross-sectional recess and port.
Figure 8:
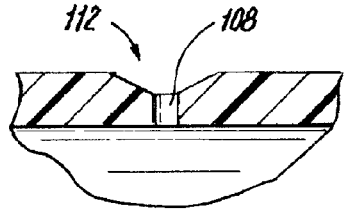
FIG. 8 is an enlarged cross-sectional view of the inner tube in accordance with the principles of the present disclosure taken along section line 7-7 of FIG. 6 illustrating an optional trapezoidal cross-sectional recess and port.
Figure 9:
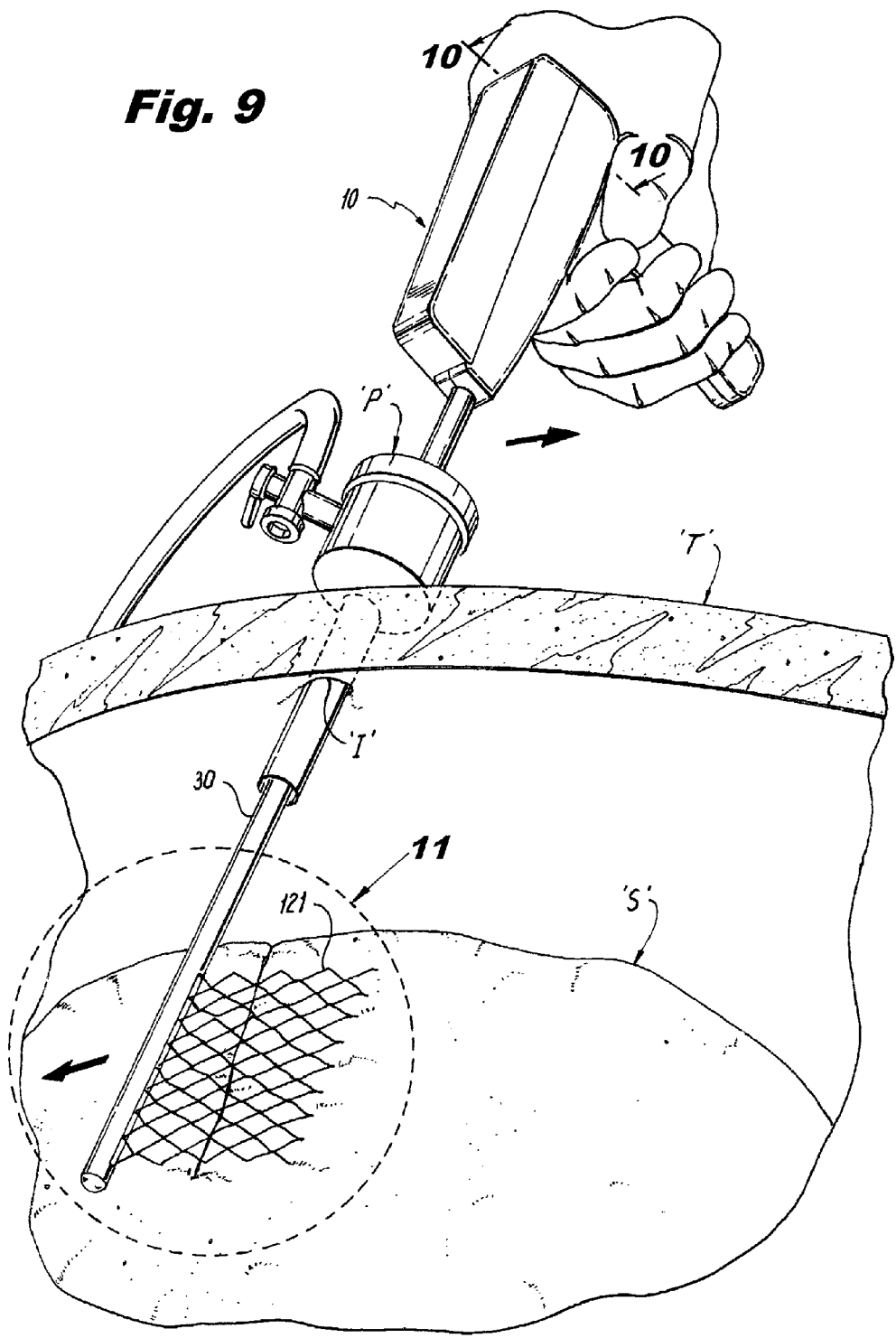
FIG. 9 is a partial cut-away view of the surgical mesh maker applicator inserted through a surgical port to apply a surgical mesh layer over a split in subdermal tissue.
Figure 10:
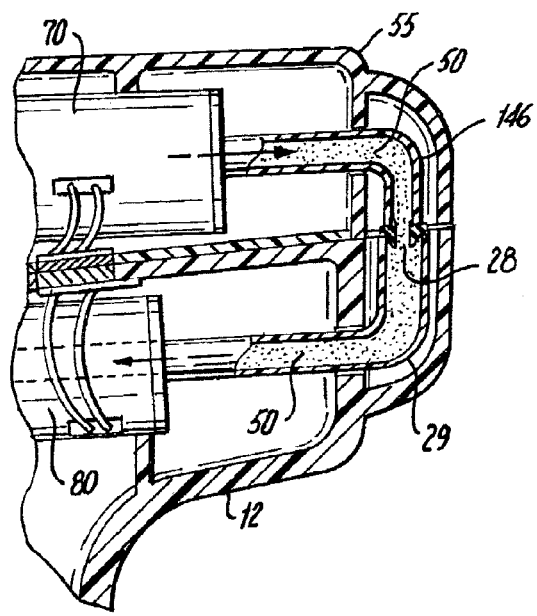
FIG. 10 is a side cross-sectional view of the surgical mesh maker applicator taken along section line 10-10 of FIG. 9.
Figure 11:
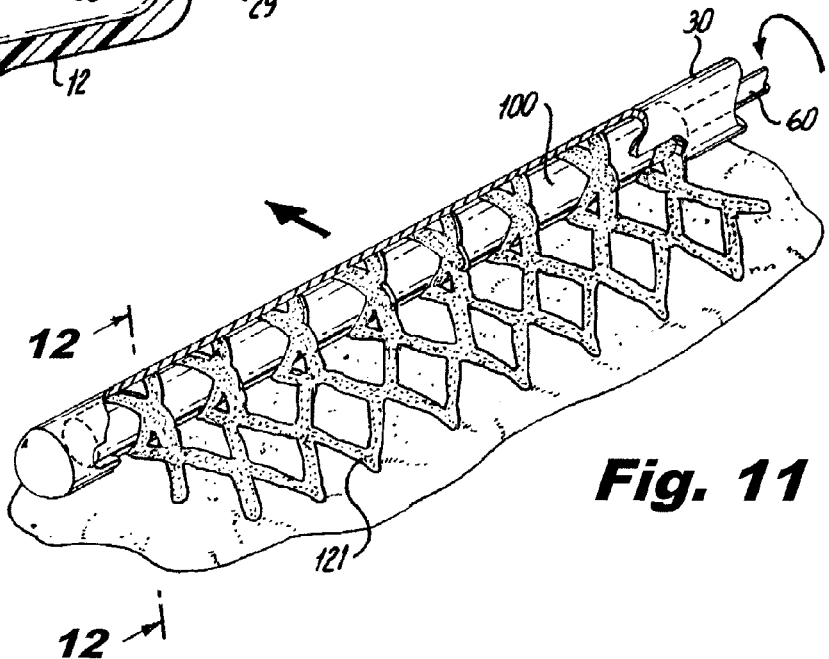
FIG. 11 is an enlarged cut-away view illustrating the flow of a in situ forming material being applied to subdermal tissue taken at the indicated area of FIG. 9.
Figure 12:
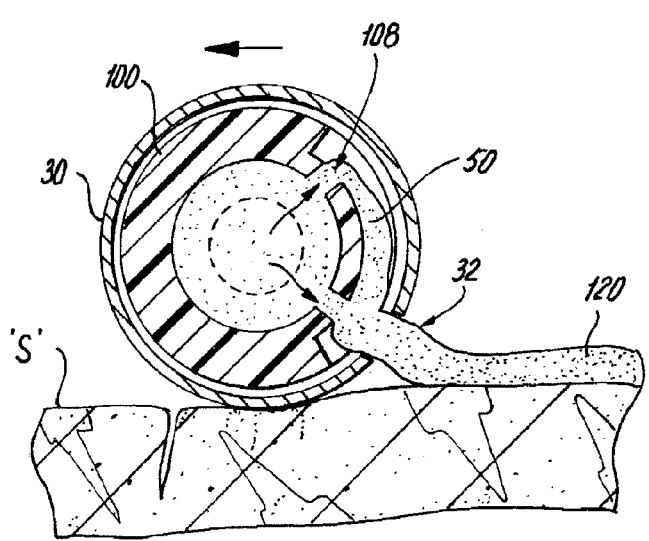
FIG. 12 is an enlarged cross-sectional view of the inner tube and outer tube forming and applying the in situ forming material to subdermal tissue taken along section line 12-12 of FIG. 11.

As disclosed, the recessed pattern 110 has a rectangular cross-sectional shape, as shown in FIG. 7. Optionally the inner member or roller 100 may have another recessed shape, e.g., the trapezoidal recess 112 shown in FIG. 8.

With reference to FIGS. 9-12, the surgical mesh maker applicator 10 uses the in situ forming material 50 from inside of the cartridge 55 to produce a patterned structure 120, e.g., a mesh 121, for strengthening the sub-dermal tissue layer CS'. With specific reference to FIG. 10, the in situ forming material 50 is shown as being forced from through the cartridge duct 146 and the housing duct 29 by the actuation mechanism 70. As discussed above, the housing duct 29 is operatively connected with the inner tube 60, which is coupled with the inner member or roller 100.

The in situ forming material 50 is expelled through the series of ports 108 and into the recessed pattern 110 allowing the in situ forming material 50 to form the patterned structure 120, which is a tacky solid, within the recessed pattern 110. The patterned structure 120 is expelled from the longitudinal slot 32 to adhere to the sub-dermal tissue 'S'.

With continued reference to FIGS. 9-12, a method of use of the surgical mesh maker applicator 10 to repair weakened sub-dermal tissue 'S' of a patient is also provided. The surgeon is provided with the surgical mesh maker applicator 10. The surgeon creates an incision 'I' in the dermal tissue layer 'T' of the patient and inserts a surgical port 'P' into the incision. The surgeon provides a compressed gas to an internal tissue cavity of the patient to insufflate the internal tissue cavity. The outer tube 30 of the surgical mesh maker applicator 10 is inserted into the surgical port 'P'. The in situ forming material 50 is applied to the sub-dermal tissue 'S' in the form of a patterned structure 120.

Figure 13:
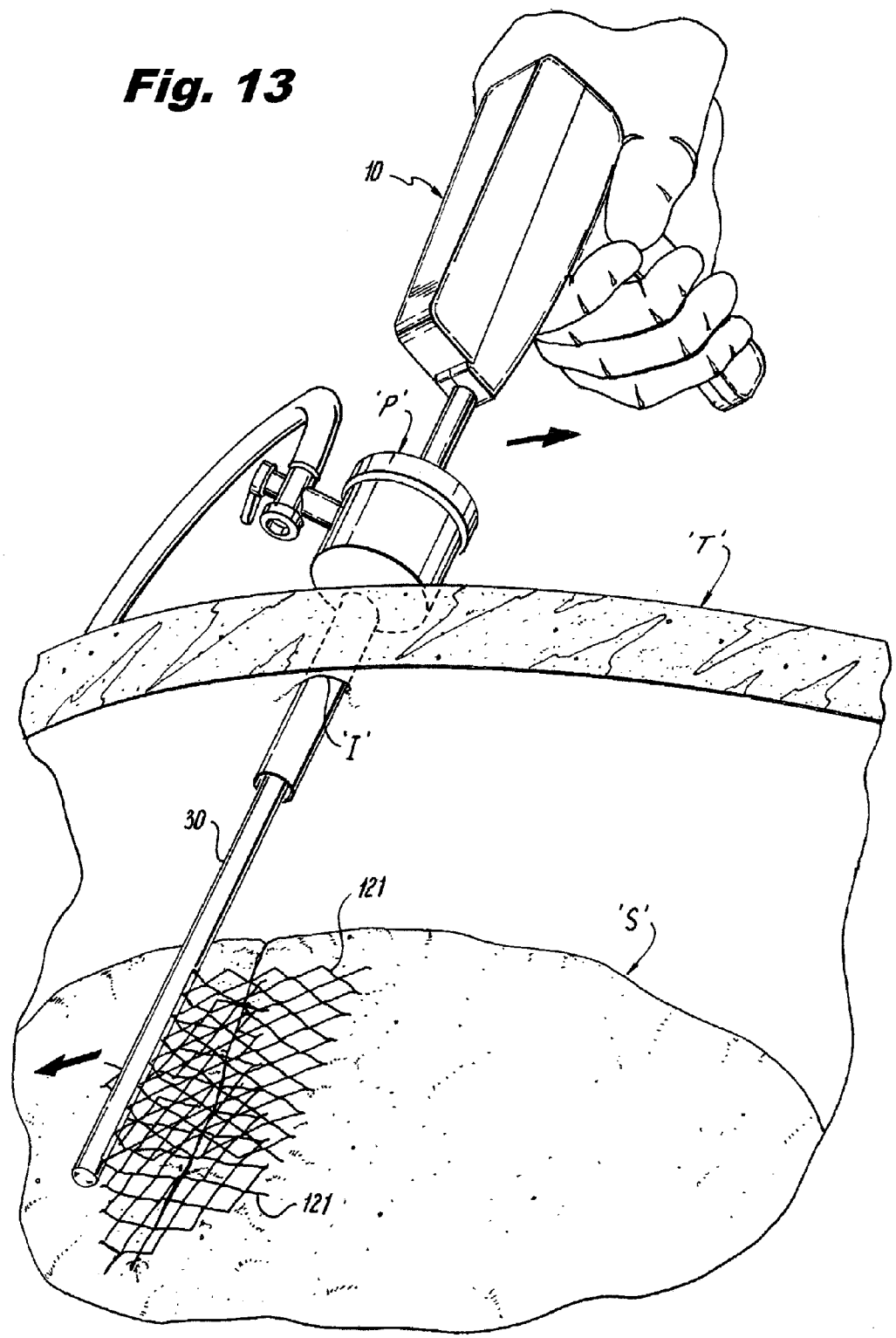
FIG. 13 is a perspective cut-away view of the surgical mesh maker applicator inserted through a surgical port to apply multiple surgical mesh layers over a single split in subdermal tissue.

Referring now to FIG. 13, the sub-dermal tissue 'S' may be weakened along multiple directions of a specific area. As a result, the surgeon may wish to strengthen the subdermal tissue 'S' along specific lines or in specific directions without covering the entire area. In addition, the surgeon may wish to add additional layers over a specific area to tailor the strengthening structure or mesh 121 to the specific need of the sub-dermal tissue 'S'. The surgical mesh maker applicator 10 is shown applying multiple layers of the mesh 121 to the sub-dermal tissue layer 'S'.

Figure 14:
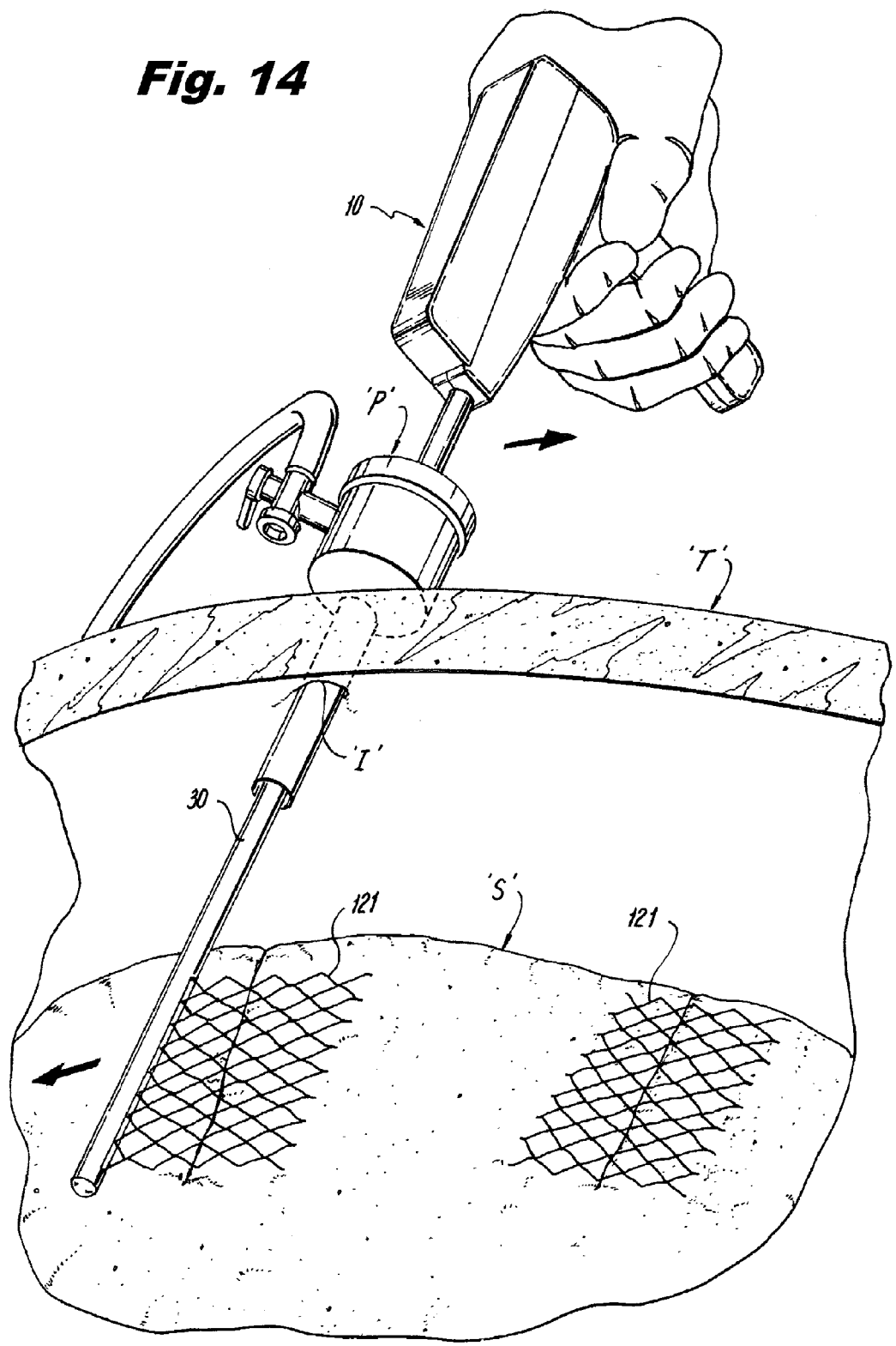
FIG. 14 is a perspective cut-away view of the surgical mesh maker applicator inserted through a surgical port to apply a multiple surgical mesh layer over multiple splits in subdermal tissue.

Referring now to FIG. 14, the sub-dermal tissue 'S' may be weakened along multiple area. As a result, the surgeon may wish to strengthen the sub-dermal tissue 'S' in specific areas without covering the entire area. The surgical mesh maker applicator 10 is shown applying the mesh 121 to a variety of separate and specific areas of the sub-dermal tissue layer 'S'.

Figure 15:
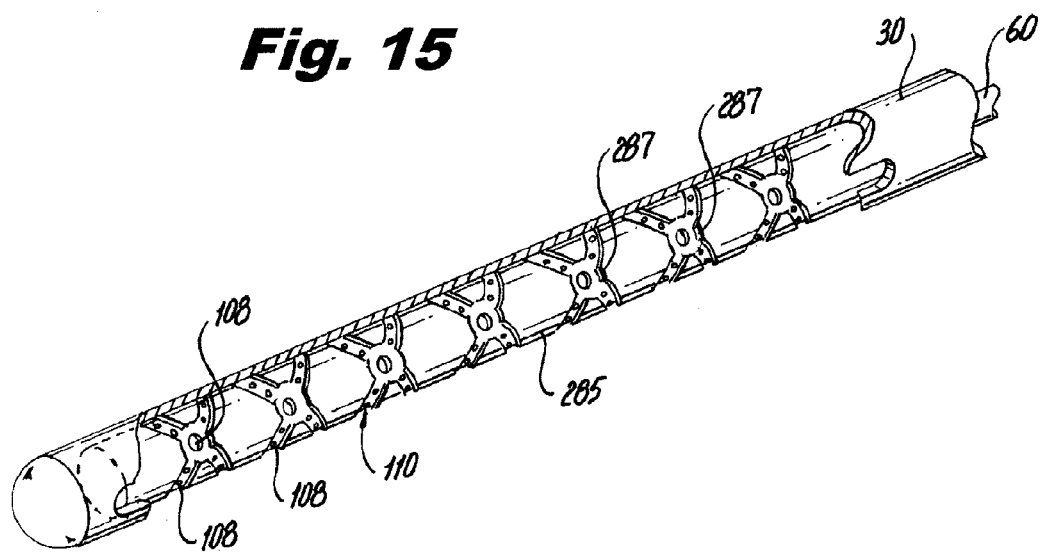
FIG. 15 is a partial cut-away view illustrating another embodiment of an inner tube within the outer tube.
Figure 16:
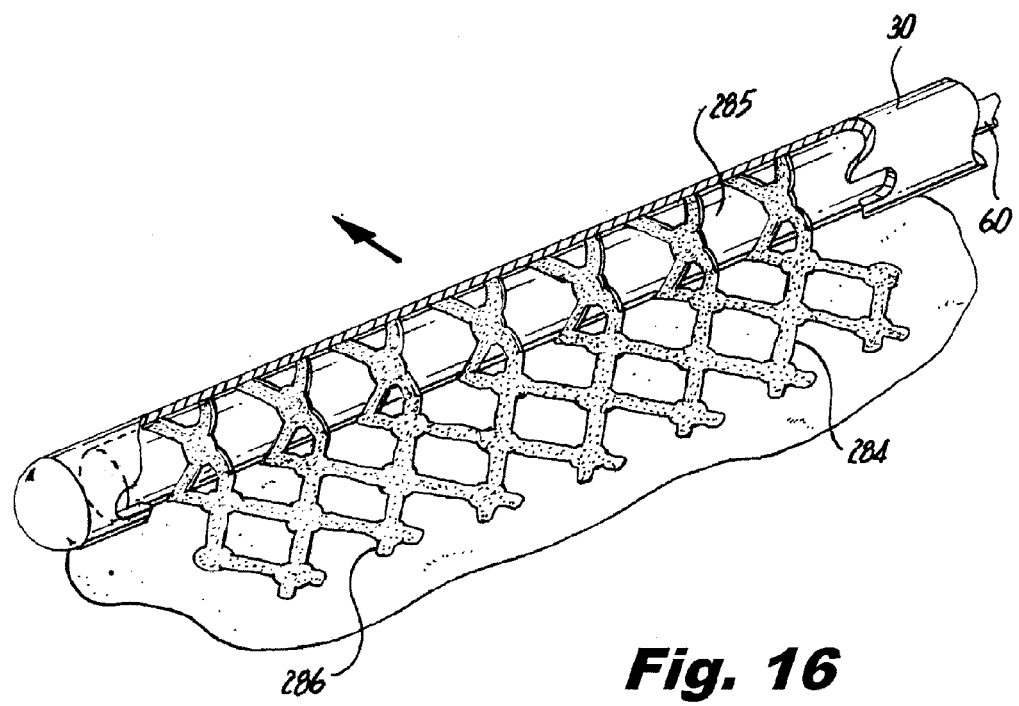
FIG. 16 is a partial cut-away view illustrating the in situ mesh pattern created by the inner tube of FIG. 15.

In another embodiment, the inner member or roller 285 defines a recessed pattern 110 that includes a circular intersection 287, as shown in FIGS. 15 and 16. Inner member or roller 285 creates a patterned structure 284, which is a mesh 286. The mesh 286 may be reinforced through the addition of fiberglass, organic fibers or in-organic fibers to the in-situ forming material. The circular intersection 287 allows additional in situ forming material 50 to collect at the circular intersections 287 of the mesh 286. The additional in situ forming material 50 strengthens the mesh 286 by substantially eliminating the sharp corners at the intersections of the mesh 286.

Figure 17:
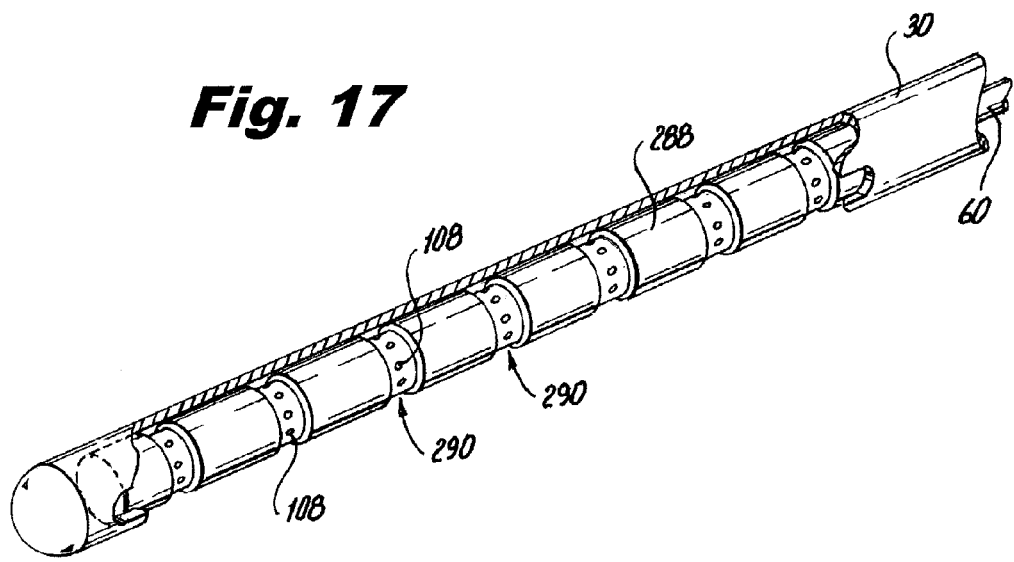
FIG. 17 is a partial cut-away view illustrating another embodiment of an inner tube within the outer tube.
Figure 18:
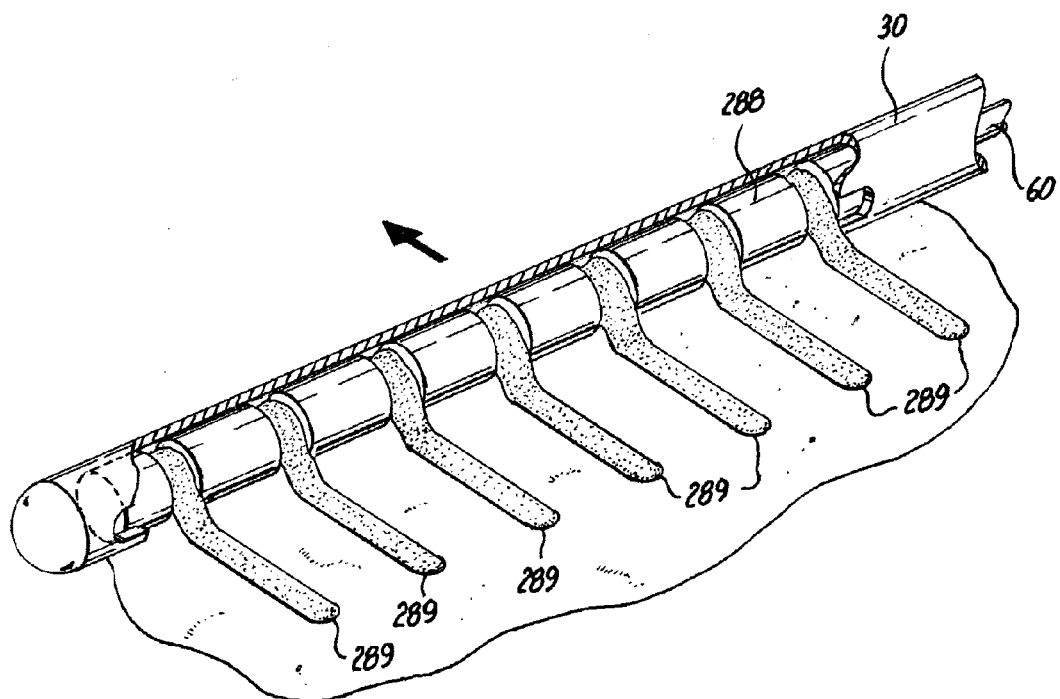
FIG. 18 is a partial cut-away view illustrating the in situ mesh pattern created by the inner tube of FIG. 17.

In still another embodiment, the inner member or roller 288 defines a series of radial recesses 290 about the inner member or roller 288, as shown in FIGS. 17 and 18. The radial recesses 290 produce a series of strips 289. The series of strips 289 allows the surgeon to provide the strengthening structure 120 in a specific direction without unnecessarily covering areas of the sub-dermal tissue 'S'.

In still another embodiment, the surgical mesh maker applicator 210 includes a first tubular portion 234 and a second tubular portion 235 that can be coupled and uncoupled from the first tubular portion 234 to allow replacement of the second tubular portion 235, as shown in FIGS. 19 and 20. The first tubular portion 234 is at least partially supported by the handle 20. The surgical mesh maker 210 includes a conduit 230 that supplies the in situ forming material 50 to the inner tube 260, through a coupling 220 held in place with respect to the conduit 230 by a collar 236. The coupling 220 forms a seal with the inner tube 260.

The first tubular portion 234 includes a pair of extrusions 238. The second tubular portion 235 defines a pair of grooves 237. The grooves 237 are sized and shaped to allow the extrusions 238 to enter into the grooves 237 and rotate into a position that prevents uncoupling of the first tubular portion 234 and the second tubular portion 235. Together the extrusions 238 and the grooves 237 form a bayonet twist lock.

Figure 21:
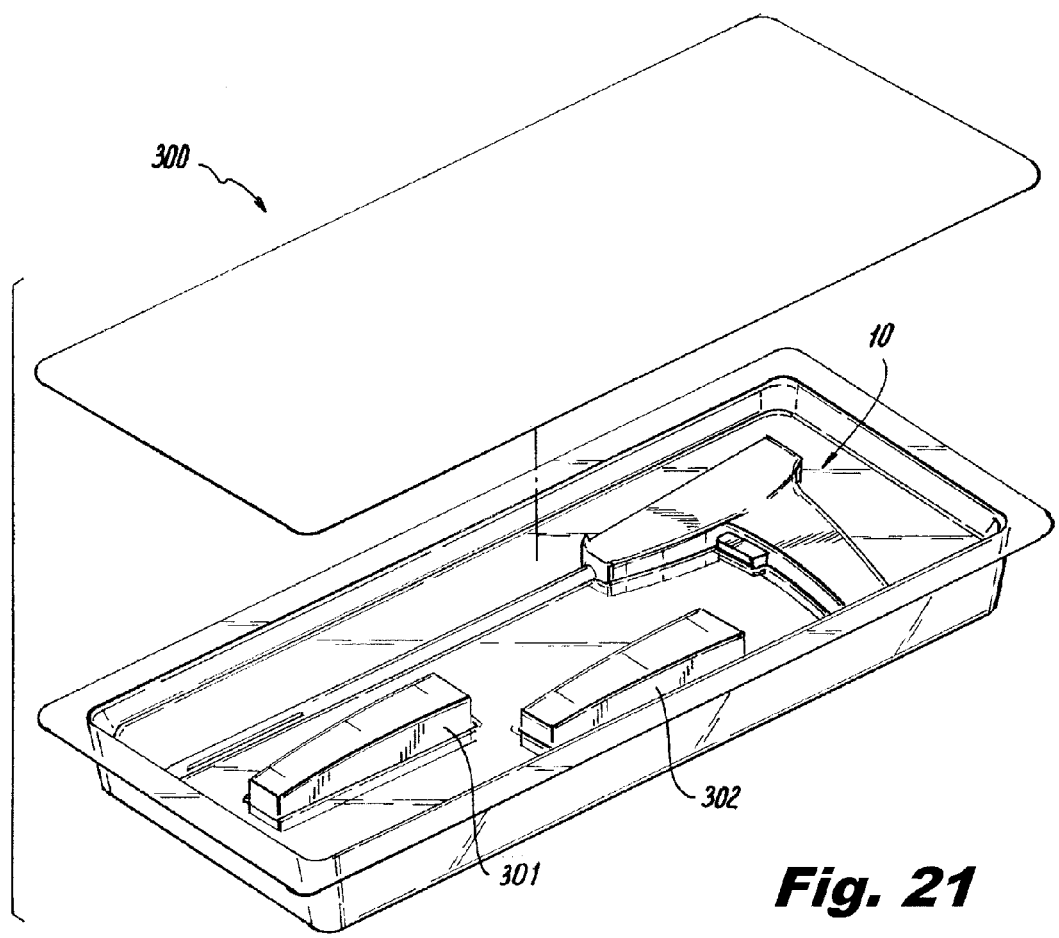
FIG. 21 is a view of the surgical mesh maker applicator in a kit including removable cartridges.

With reference to FIG. 21, the surgical mesh maker applicator 10 is provided in the form of a kit 300 that includes a first cartridge 301 and a second cartridge 302.

Figure 22:
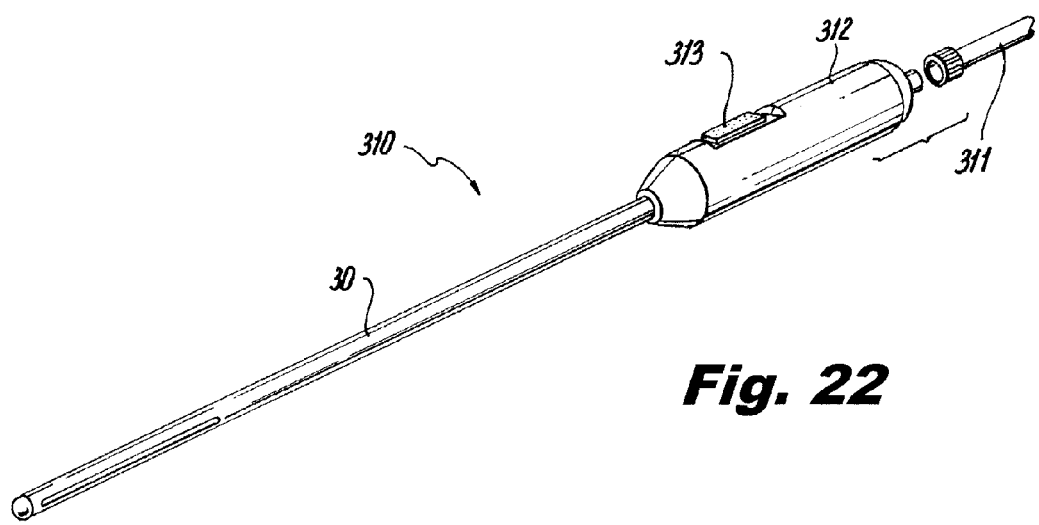
FIG. 22 is a view of another embodiment of the surgical mesh maker applicator.

With reference to FIG. 22, another embodiment of the surgical mesh maker applicator 310 is provided.

As with previous embodiments, surgical mesh maker applicator 310 generally includes the actuation mechanism 70, the rotational mechanism 80, the inner tube 60, the inner member or roller 100, and outer tube 30. These components function and are assembled together and operate in a substantially identical manner to that described herein above with regard to the prior embodiments. However, in this particular embodiment, the in situ forming material 50 is supplied by an external in situ forming material source 311. Therefore, the cylindrical handle 312 may be relatively smaller than the handle 20 and cartridge 55 combination. As disclosed, the cylindrical handle 312 has a switch 313 to actuate the surgical mesh maker applicator 310.

Figure 23:
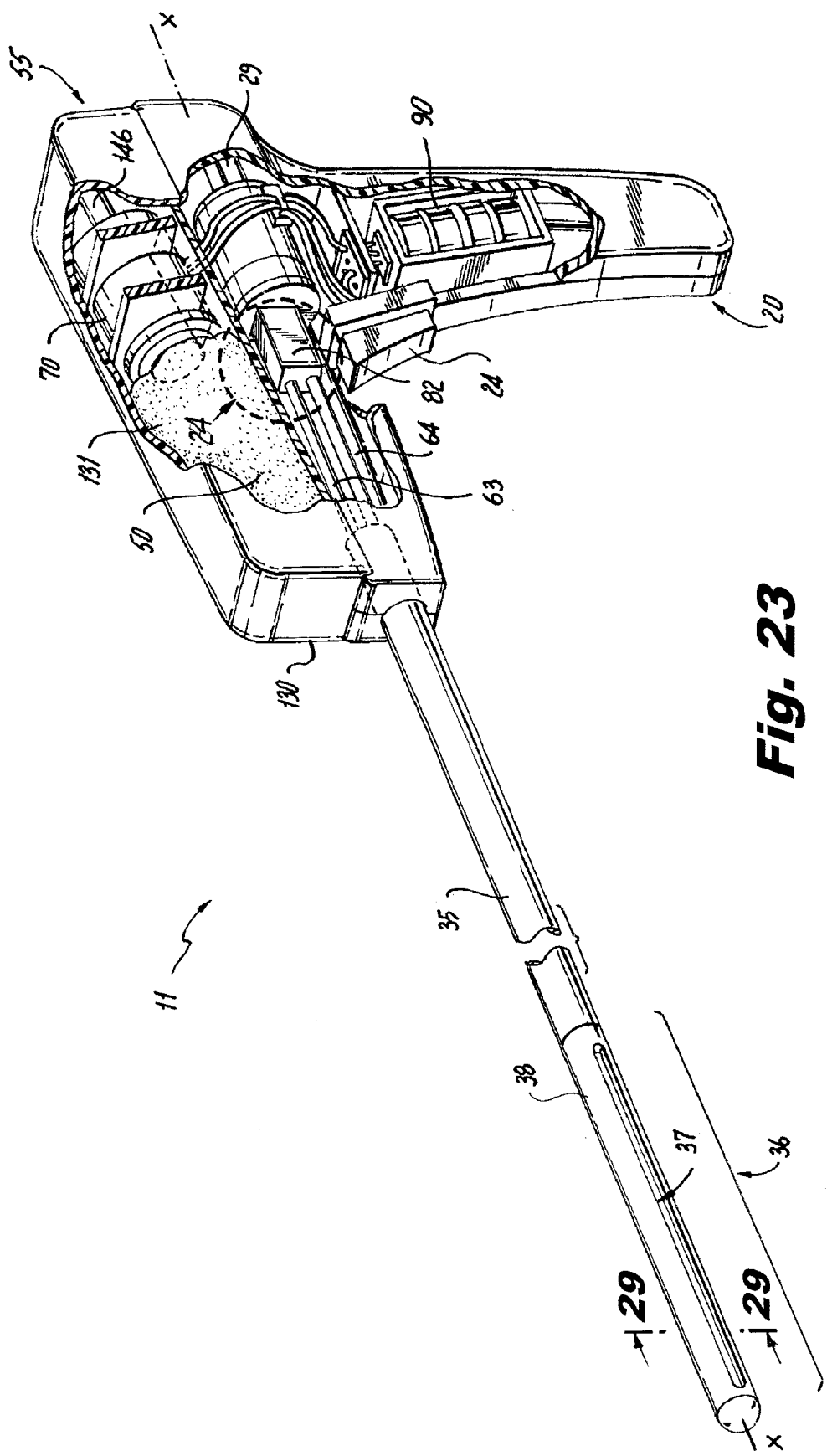
FIG. 23 is a partial cut-away view of another embodiment of a surgical mesh maker applicator illustrating an oscillating mechanism and a pair of feeder tubes.

In another embodiment shown in FIG. 23, a surgical mesh maker applicator 11 for applying an in situ forming material to sub-dermal tissue layer. Surgical mesh maker applicator 11 is substantially similar to access assembly 10 described hereinabove, and will only be described as relates to the differences therebetween.

Figure 25:
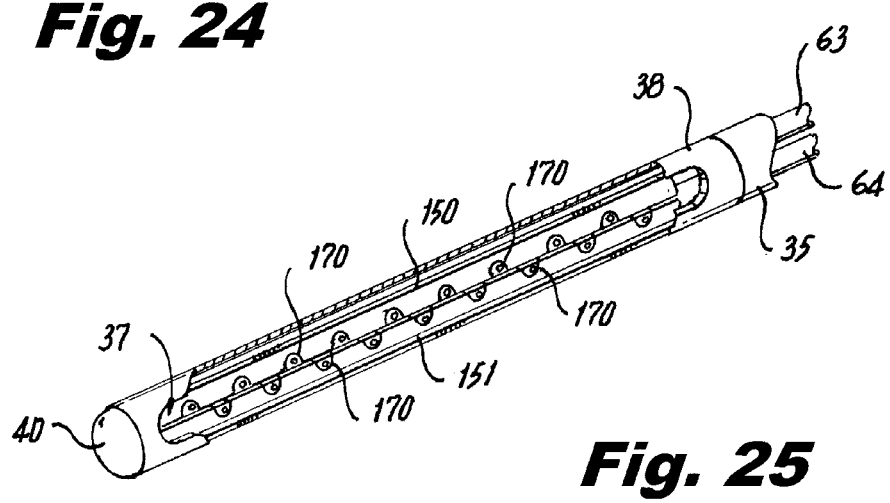
FIG. 25 is a partial cut-away view of the surgical mesh maker applicator of FIG. 23 illustrating a pair of oscillating arms located within a cover.
Figure 29:
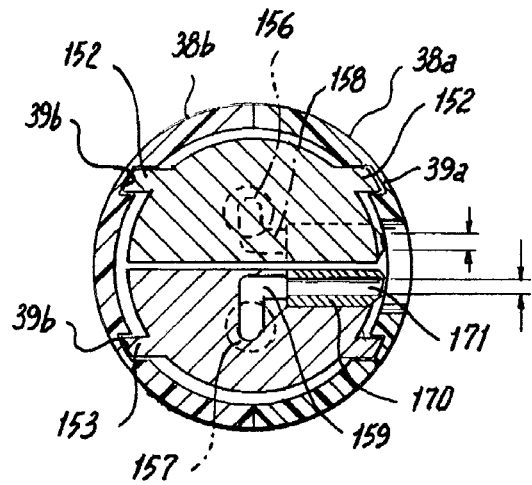
FIG. 29 is a front cross-sectional view of the oscillating arms located within the cover taken along section line 29-29 of FIG. 23.
Figure 26:
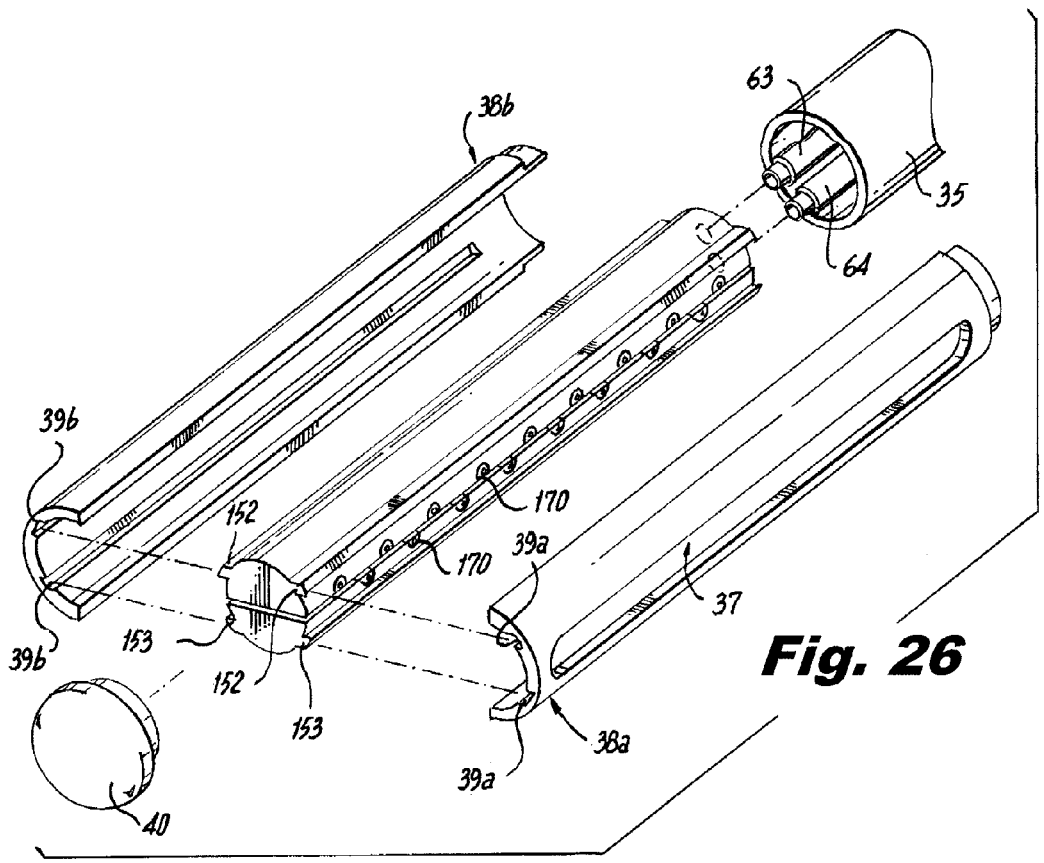
FIG. 26 is an exploded view of the distal portion of the in situ surgical mesh maker of FIG. 23 illustrating the cover, feeder tubes, and oscillating arms separated.
Figure 27:
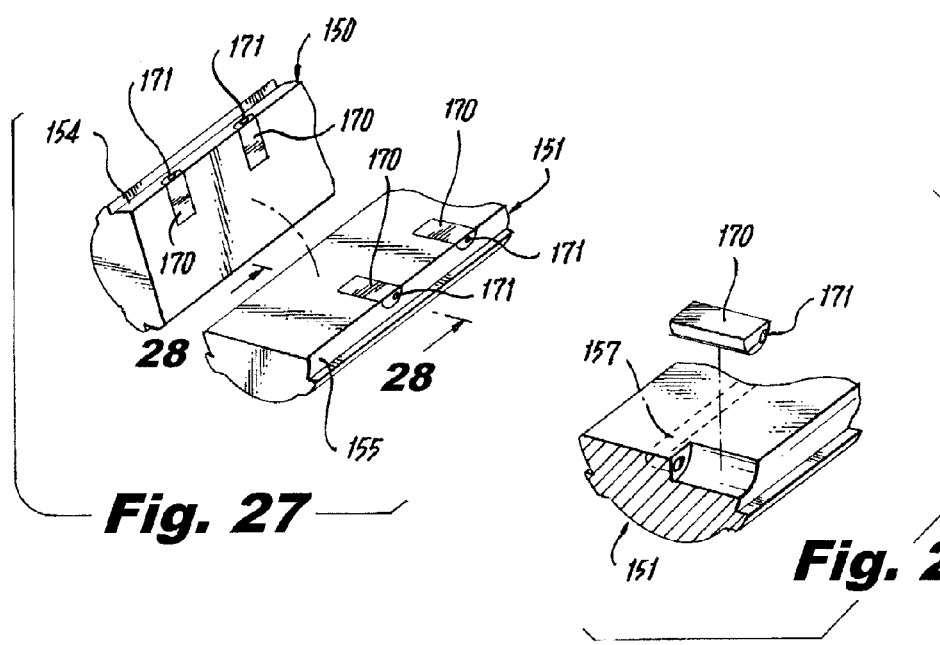
FIG. 27 an enlarged exploded view of the oscillating arms of the surgical mesh maker applicator of FIG. 23 illustrating the oscillating arms separated.
Figure 28:
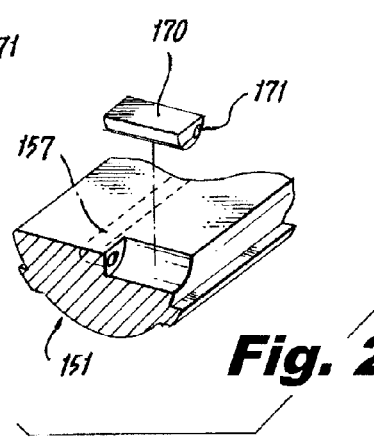
FIG. 28 is a partial, exploded cut-away view of one of the oscillating arms taken along section line 28-28 of FIG. 27, illustrating a nozzle separated from the oscillating arm.

The surgical mesh maker applicator 11 includes a handle 20, an outer tube 35, a cap 40 (FIG. 25), and a cartridge 55. The outer tube 35 defines a longitudinal slot 37 along a distal portion 36 of the outer tube 35.

Figure 24:
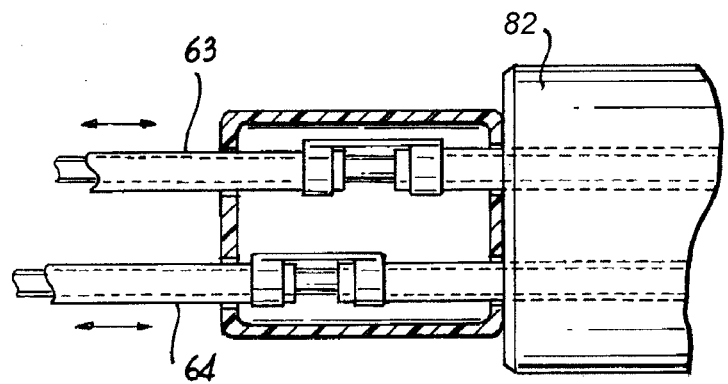
FIG. 24 is an enlarged perspective view of the oscillating mechanism and feeder tubes in accordance with the principles of FIG. 23.

The housing duct 29 is operatively connected with a first feeder tube 63 and a second feeder tube 64. The feeder tubes 63, 64 extend parallel to each other at least partially along the outer tube 35 and are connected with an oscillation mechanism 82 (FIG. 24). With additional reference to FIG. 24, the oscillation mechanism 82 translates both the first feeder tube 63 and the second feeder tube 64 in a reciprocating motion distally and proximally along the longitudinal 'X' axis.

It is envisioned that the oscillation mechanism 82 translates only one of the feeder tubes 63, 64 distally and proximally along the longitudinal 'X' axis.

The oscillation mechanism 82 and the battery pack 90 are supported within the handle 20. The battery pack 90 provides electrical power to both the actuation mechanism 70 and the oscillation mechanism 82.

With reference to FIGS. 25-29, an arm 150, 151 extends from each of the feeder tubes 63, 64. Each of the arms 150, 151 includes a pair of guides 152, 153, and defines a central passageway 156, 157. The guides 152, 153 are longitudinal protrusions that align with recesses in the outer tube 35.

The outer tube 35 includes a cover 38 along the distal portion 36. The cap 40 is coupled to the cover 38 of the outer tube 35 to form a seal with the cover 38. The cover 38 has a right hand side 38a and a left hand side 38b. Each of the right hand side 38a and left hand side 38b define a series of longitudinal slots 39a, 39b. The slots 39a, 39b align with the guides 152, 153 to provide stability to the arms 150, 151 during the reciprocating motion provided by the oscillating mechanism 82.

Each of the arms 150, 151 includes a series of nozzles 170 along an outer surface 154, 155. The series of nozzles 170 are aligned linearly along the outer surfaces 154, 155 of the arms 150, 151 and define an aperture 171 therethrough. The apertures 171 are connected with the central passageways 156, 157 through a series of arm ducts 158, 159 in each arm 150, 151. Each of the series of nozzles 170 is located along respective arms 150, 151 in such a manner to be in relatively close proximity to the series of nozzles 170 on the other arm 150, 151.

It is envisioned that each of the series of nozzles 170 are removable and replaceable to provide a variety of shaped apertures 171.

Figure 30:
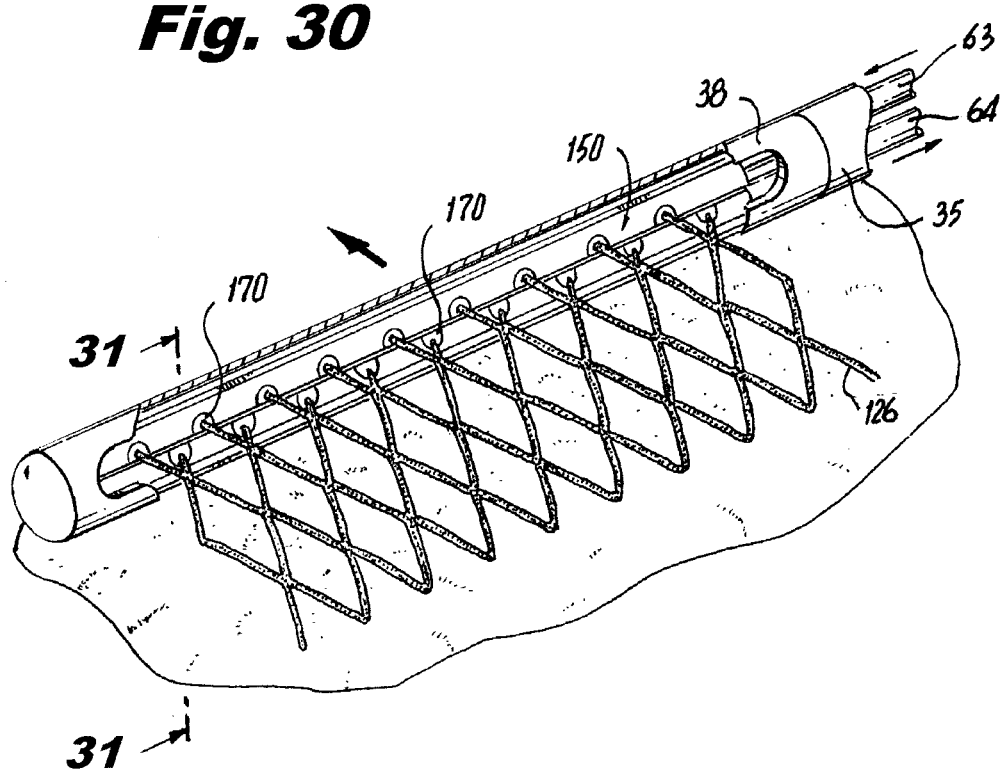
FIG. 30 is a partial cut-away view of the oscillating arms and cover forming and applying the in situ forming material to sub-dermal tissue illustrating the in situ mesh pattern created by the oscillating arms.
Figure 31:
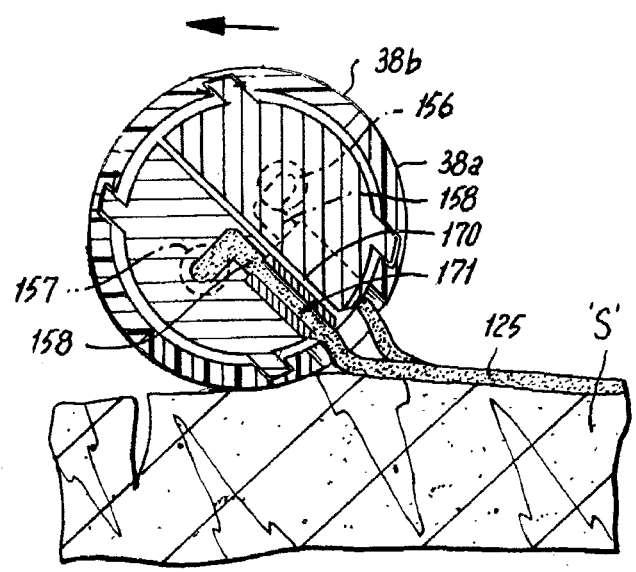
FIG. 31 is a front cross-sectional view of the oscillating arms and cover forming and applying the in situ forming material to sub-dermal tissue taken along section line 29-29 of FIG. 23.

The central passageways 156, 157 provide longitudinal passage of the in situ forming material 50 through the arms 150, 151. The series of arm ducts 158, 159 provide a path from the central passageways 156, 157 to the apertures 171 of the nozzles 170. With reference to FIGS. 30 and 31, the oscillating arms 150, 151 form the in situ forming material 50 into a patterned structure 125, e.g., a mesh 126, for strengthening the sub-dermal tissue layer 'S'. As the in situ forming material 50 is expelled from the longitudinal slot 37, the patterned structure 125 is tacky enough to allow the in situ forming material 50 to adhere to the sub-dermal tissue 'S'.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical mesh maker applicator for applying an in situ forming material to subdermal tissue, comprising:
    a handle;
    an outer tube defining a longitudinal axis and operably coupled to the handle;
    an elongated slot extending parallel to the longitudinal axis along a distal portion of the outer tube;
    an inner tube movably disposed in the outer tube, the inner tube including a plurality of openings located on a surface thereof, the inner tube rotatable with respect to the outer tube about a common axis parallel to the longitudinal axis of the outer tube; and an in situ forming material fluidly coupled to the inner tube, wherein movement of the inner tube relative to the outer tube dispenses a quantity of the in situ forming material through the plurality of openings and the elongated slot wherein the in situ forming material is a curable material.

2. The surgical mesh maker applicator of claim 1, wherein the inner tube contains a predetermined pattern.

3. The surgical mesh maker applicator of claim 2, wherein the inner tube contains a series of ports, the series of ports providing a path from an inner passageway to the predetermined pattern.

4. The surgical mesh maker applicator of claim 2, wherein the predetermined pattern is configured to dispense the in situ forming material into a mesh.

5. The surgical mesh maker applicator of claim 1, wherein the surgical mesh maker applicator further comprises a cartridge configured to retain the in situ forming material.

6. The surgical mesh maker applicator of claim 5, wherein the handle includes a retention mechanism configured to removably attach the cartridge to the handle and the cartridge includes a receiving mechanism configured to removably connect with the retention mechanism.

7. The surgical mesh maker applicator of claim 6, wherein the retention mechanism includes a stop member, the stop member limits placement of the cartridge with respect to the handle.

8. The surgical mesh maker applicator of claim 6, wherein the retention mechanism includes a projecting slide and the receiving mechanism comprises a recess configured to accept the projecting slide to removably couple the cartridge to the handle.

9. The surgical mesh maker applicator of claim 5, wherein the cartridge includes a receptor operatively connected with an actuation mechanism and the handle includes a trigger operatively connected with a transmitter, the transmitter and the receptor are in communication with each other to provide a signal to the actuation mechanism.

10. The surgical mesh maker applicator of claim 1, further comprising an actuation mechanism configured to force movement of the in situ forming material at least partially through the inner tube.

11. The surgical mesh maker applicator of claim 1, wherein the in situ forming material is selected from the group including isocyanate-based adhesives, cyanoacrylate adhesives, epoxy-based adhesives, light cured adhesives, adhesives based on CLICK chemistry, and two-component adhesives based of nucleophilic and electrophylic components.

12. The surgical mesh maker applicator of claim 1, wherein the outer tube has a first tubular portion and a second tubular portion, the first tubular portion is at least partially supported by the handle and the second tubular portion is removably joinable with the first tubular portion to allow replacement of the second tubular portion.

13. The surgical mesh maker applicator of claim 1, wherein the inner tube rotates relative to the outer tube about the longitudinal axis.

14. The surgical mesh maker applicator of claim 1, wherein the inner tube is coaxially disposed in the outer tube.

15. The surgical mesh maker applicator according to claim 1, wherein the in situ material is dispensed laterally through the elongated slot of the outer tube.

16. The surgical mesh maker applicator according to claim 1, wherein the in situ forming material exits the slot in a direction that is transverse to the longitudinal axis of the outer tube.

17. The surgical mesh maker applicator according to claim 1, wherein the elongated slot terminates proximal to the distal end of the outer tube.

* * * * *